United States Patent [19]

Franberg et al.

[11] Patent Number: 5,683,428

[45] Date of Patent: Nov. 4, 1997

[54] ATRIAL TACHYCARDIA-DETECTING HEART STIMULATOR COMPARING A PLURALITY OF P-P INTERVALS WITH A THRESHOLD

[75] Inventors: Per Franberg, Stockholm; Anders Lindgren, Taby; Hans Strandberg, Sundbyberg, all of Sweden

[73] Assignee: Pacesetter AB, Solna, Sweden

[21] Appl. No.: 571,190

[22] Filed: Dec. 12, 1995

[30] Foreign Application Priority Data

Dec. 15, 1994 [SE] Sweden ................. 9404375

[51] Int. Cl.$^6$ ............................................. A61N 1/368
[52] U.S. Cl. ................................... 607/14; 607/15
[58] Field of Search ........................... 607/14, 15

[56] References Cited

U.S. PATENT DOCUMENTS

| | | |
|---|---|---|
| 4,569,350 | 2/1986 | Mumford et al. . |
| 5,226,415 | 7/1993 | Giordo et al. ............... 607/25 |
| 5,231,985 | 8/1993 | Sutton et al. ............... 607/18 |
| 5,247,922 | 9/1993 | Stoop et al. . |
| 5,271,394 | 12/1993 | Giordo et al. ............... 607/15 |
| 5,342,405 | 8/1994 | Duncan ...................... 607/14 |
| 5,395,397 | 3/1995 | Lindgren et al. ............. 607/14 |
| 5,441,523 | 8/1995 | Nappholz .................... 607/14 |
| 5,540,725 | 7/1996 | Bornzin et al. .............. 607/9 |
| 5,540,726 | 7/1996 | Bonnet et al. ............... 607/14 |
| 5,601,613 | 2/1997 | Florio et al. ................ 607/14 |

FOREIGN PATENT DOCUMENTS

| | | |
|---|---|---|
| 0 477 878 | 4/1992 | European Pat. Off. . |
| 0 589 860 | 3/1994 | European Pat. Off. . |

*Primary Examiner*—William E. Kamm
*Assistant Examiner*—Carl H. Layno
*Attorney, Agent, or Firm*—Hill, Steadman & Simpson

[57] ABSTRACT

A heart stimulator for detecting atrial tachycardia, contains a control device to which are connected an atrial detector, having a blanking period, for detecting atrial events, a ventricular stimulation unit for delivering stimulation pulses in the ventricle, a counter for generating a variable PV interval between a detected atrial event and a stimulation pulse delivered in the ventricle, a time measurement unit for measuring time between two consecutive, detected atrial events and a calculation unit which, in a test mode for determining of whether atrial tachycardia is present, is arranged to cause the counter to generate a PV interval so the PV interval plus the atrial detector's blanking period is equal to half or less than half of an adjustable threshold level PP tachycardia. The time measurement unit sends a detection signal to the control device when a defined number of measured, consecutive PP intervals is less than a defined threshold value PP for the PP interval (threshold value PP tachycardia).

15 Claims, 1 Drawing Sheet

ATRIAL TACHYCARDIA-DETECTING HEART STIMULATOR COMPARING A PLURALITY OF P-P INTERVALS WITH A THRESHOLD

BACKGROUND OF THE INVENTION

1. Field of the Invention

The present invention relates to a heart stimulator for detecting atrial tachycardia of the type containing a control device to which are connected an atrial detector, having a blanking period, for detecting atrial events, a stimulation unit for delivering stimulation pulses in the ventricle, a counter for generating a variable PV interval between a detected atrial event and a stimulation pulse delivered in the ventricle and a time measurement unit for measuring the time between two consecutive, detected atrial events (the PP interval).

2. Description of the Prior Art

Atrial tachycardia is deemed to exist when there is regular depolarization of the atria at a rate of about 200 beats per minute (bpm) or more. Atrial tachycardia which does not include the ventricle is very common. It is not primarily life-threatening but can be very disturbing to the patient. Studies have found poorer statistical survival rates for patients with atrial tachycardia.

A dual chamber pacemaker operating in the DDD mode is connected to the heart by two electrode leads, one located in the right atrium and one placed in the right ventricle. The first D in the code designates that the pacemaker is capable of stimulating both the atrium and the ventricle. The second D means that the heart can be sensed in both the atrium and the ventricle. The third position in the mode code designates the pacemaker's mode of response. The designation D means that the pacemaker is both triggered and inhibited (dual response). In simplified terms, "triggered" means that a sensed signal triggers a stimulation pulse by the pacemaker, whereas "inhibited" means that the pacemaker's stimulation pulse is inhibited (blocked) when the pacemaker senses a heart signal. These functions depend, of course, on where the signals are sensed in the heart and when.

The rate in the atrium is determined from continuous measurement of the PP interval. A P wave designates a natural depolarization in the atrium. The PP interval is thus the time between two consecutive P waves. An A wave indicates a stimulated atrial event. The QRS complex, or R wave, indicates a natural depolarization in the ventricle. The V wave indicates a stimulated event in the ventricle.

In a dual chamber DDD pacemaker, the P wave starts a counter which imposes a PV interval, i.e. the time from a sensed P wave to a ventricular stimulation. When the frequency of the P waves increases, the stimulation rate also increases to a corresponding degree in the ventricle.

With an atrial synchronous dual chamber pacemaker, ventricular stimulation is controlled by a detected atrial event. A problem can occur with atrial-synchronous pacemakers in tachycardia. As a result, a high atrial rate could then lead to an excessively high rate of ventricular stimulation. One way to prevent this is to introduce a maximum tracking rate (MTR) which designates the highest permissible rate for ventricular stimulation. A disadvantage of such an approach, however, is that the MTR should be high when the normal sinus rate is high, i.e. during physical exertion requiring a high heart rate, but low in the presence of any pathologically rapid rate. The sinus rate is the rate generated by the heart's own pacemaker, the sinoatrial node. This rate depends, in turn, on the load to which the body is subjected.

The solution to this problem has hitherto been to have the pacemaker switch to some other operating mode (e.g. the VVI mode) with a slower (or declining) rate when the ventricular rate remains at the MTR for a long period of time, irrespective of whether such a switch is desirable. Another way to solve the problem is to have an activity sensor in the pacemaker control the MTR so the MTR is only assigned a high value when the sensor detects physical activity.

Ventricular stimulation generates powerful signals which interfere with the intended operation of the atrial detector during ventricular stimulation and for a short period of time thereafter, depending on the design of the filter and amplifier in the atrial detector. To protect the atrial detector against this interference, a blanking period is introduced for the atrial detector. This period occurs immediately after the AV interval (or PV interval, if the atrium is not stimulated). Detections are ignored during the blanking period. The blanking period must be longer than the duration of interference and can have a fixed duration or a duration adjustable by means of pacemaker programming. A common time is 75 ms, but times from 10 to 130 ms are used.

Detection of pacemaker-mediated tachycardia (PMT) is discussed in U.S. Pat. No. 4,569,350. This PMT test is performed when the rate for detected P waves exceeds a threshold value a defined number of times. The test measures the VP interval or the PP interval after a ventricular stimulation. The PV interval is varied by prolongation with an appropriate brief time Δ. PMT is present if the VP interval is unaffected or if the PP interval increases by Δ. No PMT is present if the VP interval is shortened by Δ or if the PP interval is unaffected, but some other atrial tachycardia may exist.

The PP interval must be measurable for this known device to work. The PP interval, however, cannot always be measured. Problems can develop in detecting the P wave when the P wave rate increases, since P wave could occur during the atrial detector's blanking period and pass undetected. The PP interval is generally constant over a number of consecutive intervals in regular tachycardia. But when a P wave occurs during the blanking period, the measured PP interval could actually consist of two consecutive PP intervals without any detection of the intermediate P wave.

Finding pathological rates which are definitely 200 bpm or higher (corresponding to a distance between the P waves (the PP interval) of 300 ms or less) is essential in the confirmation of the presence of atrial tachycardia.

SUMMARY OF THE INVENTION

An object of the present invention is to achieve more reliable detection of atrial tachycardia.

This object is achieved according to the invention in a heart stimulator of the initially described type which also contains a calculation unit which, in a test mode for determining whether atrial tachycardia is present, is arranged to cause the counter to generate a PV interval in which the sum of the PV interval and the atrial detector's blanking period is equal to haft or less than haft of an adjustable threshold value. The time measurement unit sends a detection signal to the control device when a defined number of measured, consecutive PP intervals is less than a defined threshold value for the PP interval.

This makes it possible, even with short PP intervals, to detect P waves which previously occurred during the atrial detector's blanking period.

This is achieved according to the invention by shortening the PV interval so the Pv interval plus the blanking period are equal to or less than haft the PP interval. In regular tachycardia, the next P wave will then be detected, since the blanking period following the shortened PV interval will have concluded before haft the PP interval has expired.

DESCRIPTION OF THE PREFERRED EMBODIMENTS

Figure 1:
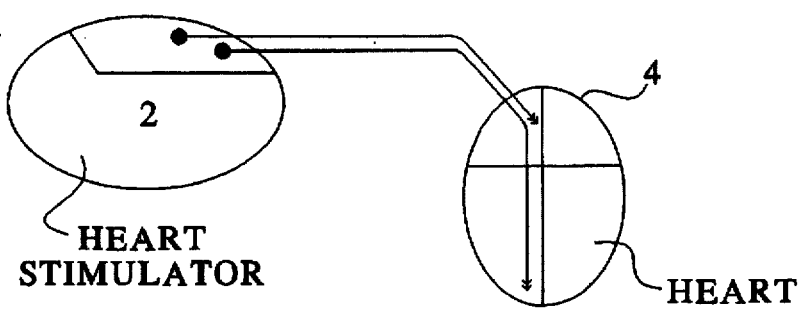
FIG. 1 schematically shows a DDD pacemaker.
Figure 2:
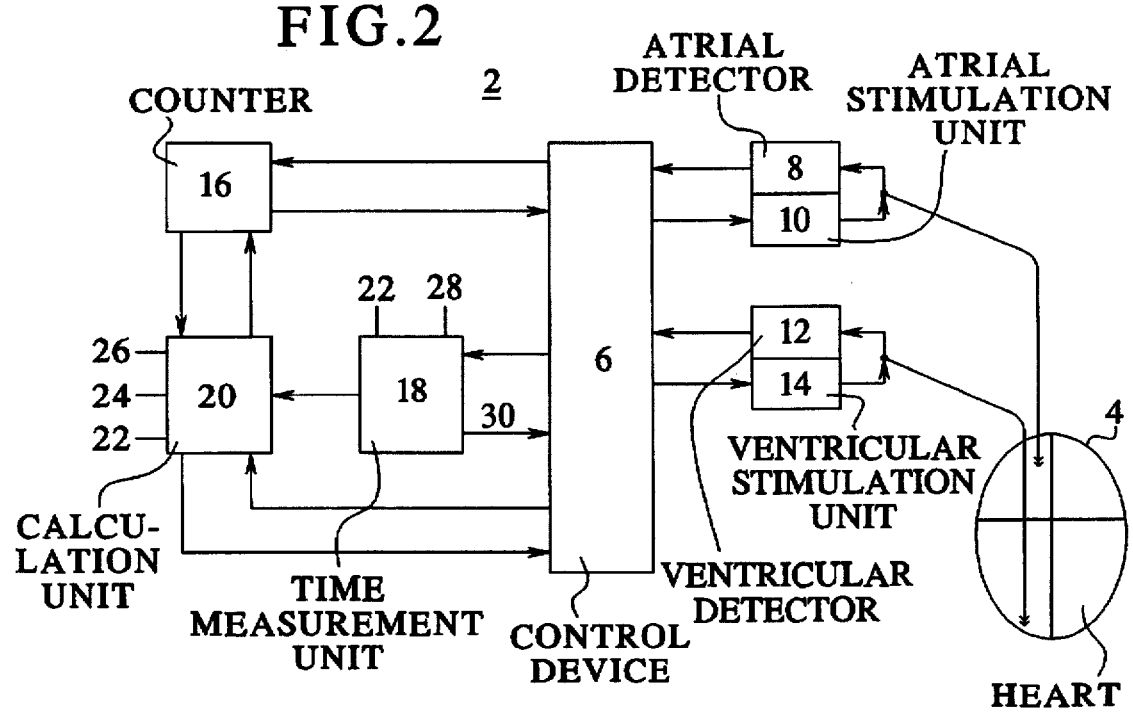
FIG. 2 is a block diagram of a DDD pacemaker with the invention implemented therein.

FIG. 1 shows a heart stimulator 2 connected to a heart 4. According to FIG. 2, the heart stimulator 2 contains a control device 6 to which an atrial detector 8, an atrial stimulation unit 10, a ventricular detector 12, a ventricular stimulation unit 14, a counter 16, arranged to generate a variable, adjustable PV interval (the time between a sensed P wave and a ventricular stimulation pulse), and a time measurement unit 18 are connected. A threshold value for the PP interval (PP tachycardia 22) can be set in the time measurement unit 18. A calculation unit 20 is connected to the counter 16, the time measurement unit 18 and the control device 6. The threshold value PP tachycardia 22, as well as values for the tachycardia test interval 24, can be set in the calculation unit 20.

The atrial detector detects atrial events and sends these signals to the control device 6 and on to the time measurement unit 18, which is arranged to measure the time between two detected, consecutive P waves, thereby obtaining a value for the PP interval.

The blanking period of the atrial detector 8 is stored in the control device 6 and can be changed when the heart stimulator is re-programmed. The duration of the blanking period is from 10 to 130 ms, preferably 75 ms.

As previously noted, the PP interval for a number of consecutive intervals is largely constant during regular tachycardia. But when a P wave occurs during the blanking period, the measured PP interval could actually consist of two consecutive PP intervals without any detection of the intermediate P wave.

When the PV interval is shortened so the PV interval plus the blanking period are less than haft the PP interval, the next P wave will be detectable. This is possible, since the blanking period following the shortened PV interval will have concluded before half the PP interval has expired, has expired, and any P interval will then be wave occurring after haft the PP interval will then be detected.

Figure 3:
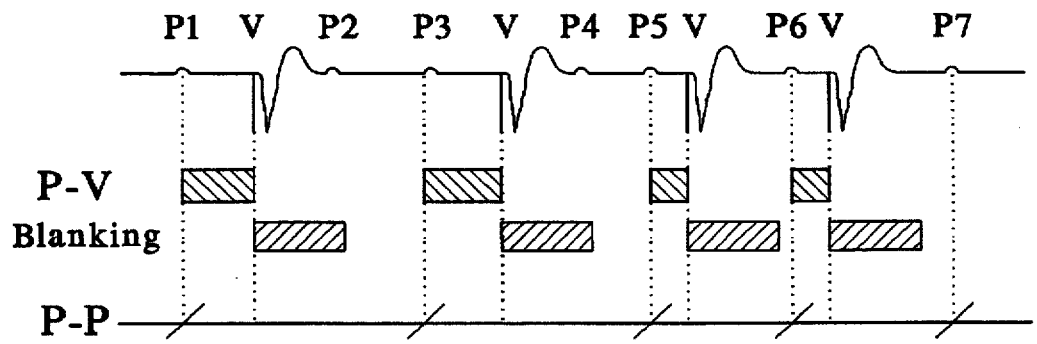
FIG. 3 is a schematic illustration of a signal sequence for the invention.

FIG. 3 shows a simplified segment of a heart's ECG signal which illustrates the invention and which illustrates the invention and depicts a situation in which a P wave occurs during the atrial detector's blanking period. FIG. 3 only provides a schematic picture of events to simplify understanding of the invention. For example, the proportions between time intervals are not precisely correct. In FIG. 3, the P1–P3 interval is sensed as a PP interval, since P2 occurs during the atrial detector's 8 blanking period. Even the P4 P wave occurs during the blanking period and therefore goes undetected. According to the invention, the PV interval following P5 is shortened, so P6 can be detected.

To prevent needless testing, a tachycardia test interval 24 is stored in the calculation unit 20. A specific number, i.e. from one to five, e.g. two, of PP intervals must be shorter than the tachycardia test interval 24 for a tachycardia test to be performed. This adjustable number 26 can be set in the calculation unit 20.

The tachycardia test interval 24 can either be preset, then being subject to change during re-programming, or can be dependent on the PV interval in such a way that the tachycardia test interval 24 consists of about twice the sum of the existing PV interval and the blanking period. As a result of, e.g., time constants for component parts (amplifier, counter etc.), some tolerance is allowed for the tachycardia test interval. This means that the sum of the existing PV interval and the blanking period is multiplied by a factor in the range of 1.8 to 2.2 range.

The tachycardia test will be performed when the PP interval is shorter than the tachycardia test interval 24 the defined number of times 26. This means that the PV interval will be shortened in the counter 16 so the PV interval plus the blanking period are equal to haft or less than haft of an adjustable threshold value, referred to as PP tachycardia 22.

If the PP interval is still shorter than the threshold value PP tachycardia 22 after an additional defined number 28 of consecutive PP intervals, whose value may be two or more, e.g. four, atrial tachycardia will be deemed to exist, and the time measurement unit 18 will send a detection signal 30 to the control device 6. This additional defined number 28 is set in the time measuring unit 18. In the calculation of the number of PP intervals shorter than the threshold value for PP tachycardia 22, initial PP intervals, i.e. occurring before the tachycardia test began, and which are shorter than the tachycardia test interval 24, are also counted, if they were less than the threshold value PP tachycardia 22.

The tachycardia test stops immediately when any PP interval exceeds the threshold value PP tachycardia 22 and is not repeated until the conditions noted above have been met, i.e. when a number 26 of consecutive PP intervals, for example two, is shorter than the tachycardia test interval.

When atrial tachycardia has been detected by the heart stimulator 2 according to the invention, the heart stimulator 2 can, e.g., continue at the rate the heart had before the tachycardia started or slowly reduce the rate to some other suitable value. During the tachycardia, having the heart stimulator switch to a non-P-synchronous mode, such as VVI or DDI, with or with out rate response, may be appropriate.

As noted above, there is an upper rate limit (MTR) for the stimulation rate in the ventricle and an attendant MTR interval which is the shortest permissible time between ventricular stimulation pulses. Since a shortening of the PV interval means that ventricular stimulation will occur earlier, the MTR interval may not have time to expire. The MTR interval should be set at the time the heart stimulator 2 is programmed, and this setting and implementation of the various options, described below, will be made in the control device 6. Two different situations could then develop (in the following, the threshold value PP tachycardia 22 has been assigned a value of 300 ms and the blanking period a value of 75 ms to increase understanding of the invention).

In the first instance, the MTR interval expires before the heart stimulator 2 is to stimulate the heart after the shortened PV interval. Detection of the tachycardia is then very rapid. In the example with a tachycardia test interval of 300 ms, detection takes 4×300 ms=1.2 seconds. Thus four consecutive PP intervals will be the threshold value PP tachycardia (300 ms).

In the second instance, no stimulation is delivered to the ventricle after the shortened PV interval, since the MTR interval has not expired and the MTR interval may not be exceeded. The shortened PV interval (75 ms) expires, stimulation is inhibited if the MTR interval has not expired when it is time for the heart stimulator to stimulate and a 225 ms VA interval starts. Two situations could then occur:

In the first, a new P wave could be detected within this time frame. The pacemaker would then start a new, shortened PV interval (75 ms), leaving scope for reliable detection of the tachycardia.

In the second, no new P wave is detected within this time frame (the VA interval). The pacemaker will then stimulate in the atrium, producing a PA time of 300 ms. A normal AV interval is then imposed, thereby concluding the tachycardia test. In the worst instance, the W interval, i.e. the time between consecutive ventricular stimulation pulses, could increase by 300 ms. According to this example, this is equivalent to a reduction in the stimulation rate from e.g. 120 to 75 pulses per minute (ppm) but only for one beat. Occasional rhythm deviations have no notable hemodynamic impact and often go unnoticed by the patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:
   atrial detector means adapted for interacting with a patient for detecting atrial events in said patient, said atrial detector means having a blanking period during which any detected atrial events are ignored;
   ventricular stimulation means for emitting ventricular stimulation pulses and adapted for delivering said ventricular stimulation pulses to said patient;
   interval setting means for generating a variable PV interval between an atrial event detected by said atrial detector means and emission of a next one of said ventricular stimulation pulses by said ventricular stimulation means for causing said ventricular stimulation means to emit said next one of said ventricular pulses at an end of Said variable PV interval;
   time measurement means for measuring a PP interval between two consecutive atrial events detected by said atrial detector means; and
   means for detecting whether atrial tachycardia is present in said patient including means for causing said interval setting means to generate a set PV interval such that a sum of said set PV interval and said blanking period is less than or equal to an adjustable threshold value, and for placing said time measurement means in a mode for emitting a signal indicating the presence of atrial tachycardia if each of a defined plurality of consecutive PP intervals measured by said time measurement means is less than said adjustable threshold value.

2. A heart stimulator as claimed in claim 1 wherein said interval setting means comprises a counter.

3. A heart stimulator as claimed in claim 1 wherein said means for detecting whether atrial tachycardia is present further includes means for receiving a tachycardia test interval and wherein said means for detecting whether atrial tachycardia is present comprises means for detecting whether atrial tachycardia is present only when one PP interval is less than said tachycardia test interval.

4. A heart stimulator as claimed in claim 3 wherein said means for receiving a tachycardia test interval comprises means for receiving a tachycardia test interval comprising approximately twice a sum of a current PV interval and said blanking period.

5. A heart stimulator as claimed in claim 3 wherein said means for receiving a tachycardia test interval comprises means for receiving a tachycardia test interval comprising an adjustable, constant value.

6. A heart stimulator as claimed in claim 1 wherein said means for detecting whether atrial tachycardia is present further includes means for receiving a tachycardia test interval and wherein said means for detecting whether atrial tachycardia is present comprises means for detecting whether atrial tachycardia is present only when a specified number of PP intervals is less than said tachycardia test interval.

7. A heart stimulator as claimed in claim 6 wherein said means for receiving a tachycardia test interval comprises means for receiving a tachycardia test interval comprising approximately twice a sum of a current PV interval and said blanking period.

8. A heart stimulator as claimed in claim 6 wherein said means for receiving a tachycardia test interval comprises means for receiving a tachycardia test interval comprising an adjustable, constant value.

9. A method for detecting atrial tachycardia in a patient comprising the steps of:
   detecting atrial events in said patient, and ignoring any atrial events detected during a blanking period;
   emitting ventricular stimulation pulses and delivering said ventricular stimulation pulses to said patient;
   generating a variable PV interval between an atrial event and emission of a next one of said ventricular stimulation pulses and emitting said next one of said ventricular stimulation pulses at an end of said variable PV interval;
   measuring a PP interval between two consecutive atrial events;
   generating a set PV interval such that a sum of said set PV interval and said blanking period is less than or equal to an adjustable threshold value; and
   emitting a signal indicating the presence of atrial tachycardia if each of a defined plurality of consecutive PP intervals is less than said adjustable threshold value.

10. A method as claimed in claim 9 comprising the additional steps of:
    setting a tachycardia test interval; and
    detecting whether atrial tachycardia is present only when one PP interval is less than said tachycardia test interval.

11. A method as claimed in claim 10 wherein the step of setting a tachycardia test interval comprises setting a tachycardia test interval comprising approximately twice a sum of a current PV interval and said blanking period.

12. A method as claimed in claim 10 wherein the step of setting a tachycardia test interval comprises setting a tachycardia test interval comprising an adjustable, constant value.

13. A method as claimed in claim 9 comprising the additional steps of:
    setting a tachycardia test interval; and
    detecting whether atrial tachycardia is present only when a specified number of PP intervals is less than said tachycardia test interval.

14. A method as claimed in claim 13 wherein the step of setting a tachycardia test interval comprises setting a tachycardia test interval comprising approximately twice a sum of a current PV interval and said blanking period.

15. A method as claimed in claim 13 wherein the step of setting a tachycardia test interval comprises setting a tachycardia test interval comprising an adjustable, constant value.

* * * * *